United States Patent [19]

Diedrich et al.

[11] Patent Number: 4,665,058
[45] Date of Patent: May 12, 1987

[54] COMPOSITIONS AND METHOD OF TREATMENT FOR SICKLE CELL ANEMIA

[75] Inventors: Donald F. Diedrich; Christopher L. Maynard, both of Lexington, Ky.

[73] Assignee: The University of Kentucky Research Foundation, Lexington, Ky.

[21] Appl. No.: 712,616

[22] Filed: Mar. 16, 1985

[51] Int. Cl.⁴ .............................................. A61K 31/70
[52] U.S. Cl. ...................................... 514/25; 514/815; 536/4.1
[58] Field of Search ..................... 514/25, 815; 536/4.1

[56] References Cited

U.S. PATENT DOCUMENTS 3,833,724 9/1974 Cerami et al. ....................... 424/129

OTHER PUBLICATIONS

Raper–Ann. Soc. Belge Med. Trop., 1969, 49, 2, 205–210.
Chang, et al, "Comparative Evaluation of Fifteen Anti--Sickling Agents", 1983, pp. 693–704.
Levine, et al, "Cetiedil Inhibition of Calmodulin-Stimulated Enzyme Activity", 1984, pp. 581–584.
Clark, et al, "Hydration of Sickle Cells Using the Sodium Ionophore Monensin", 1982, pp. 1074–1080.

*Primary Examiner*—Frederick E. Waddell
*Attorney, Agent, or Firm*—King and Schickli

[57] ABSTRACT

The invention provides a new composition and method for the treatment of sickle cell anemia. The composition includes as an active ingredient an effective amount of the compound, phlorizin benzylazide:

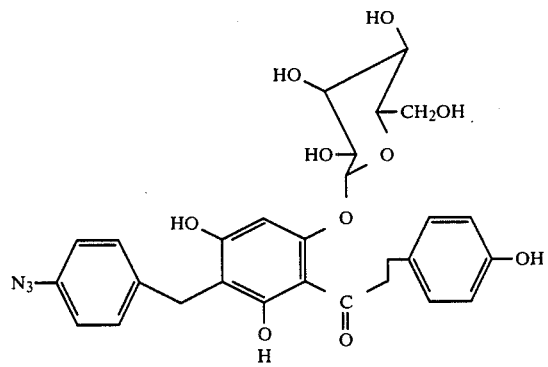

and an appropriate pharmaceutical excipient. Load and maintenance dosage ranges as well as effective blood concentration levels for the active ingredient are disclosed.

14 Claims, 5 Drawing Figures

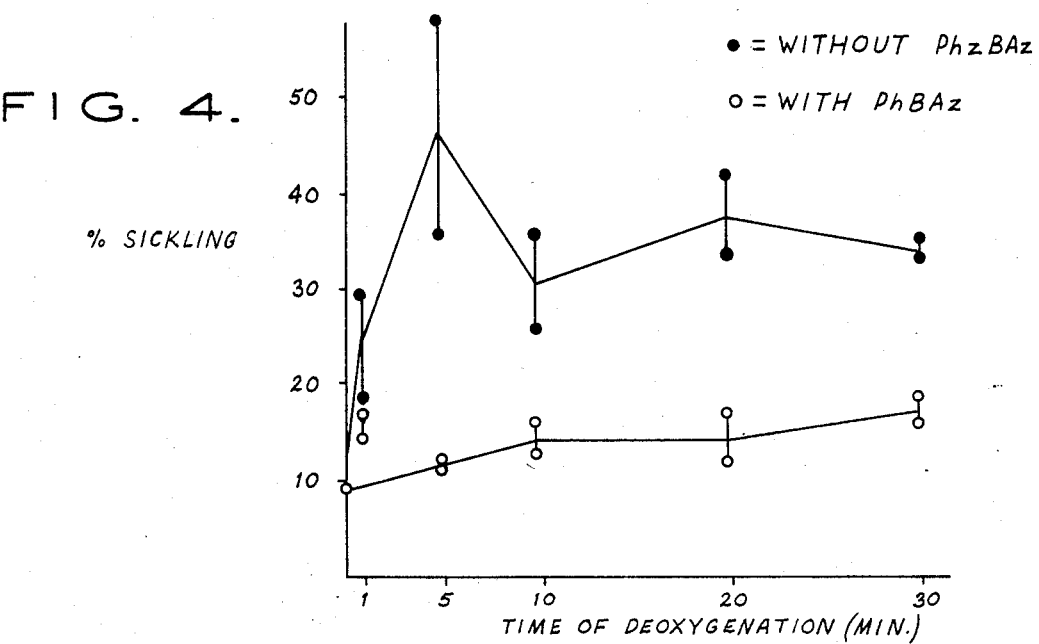
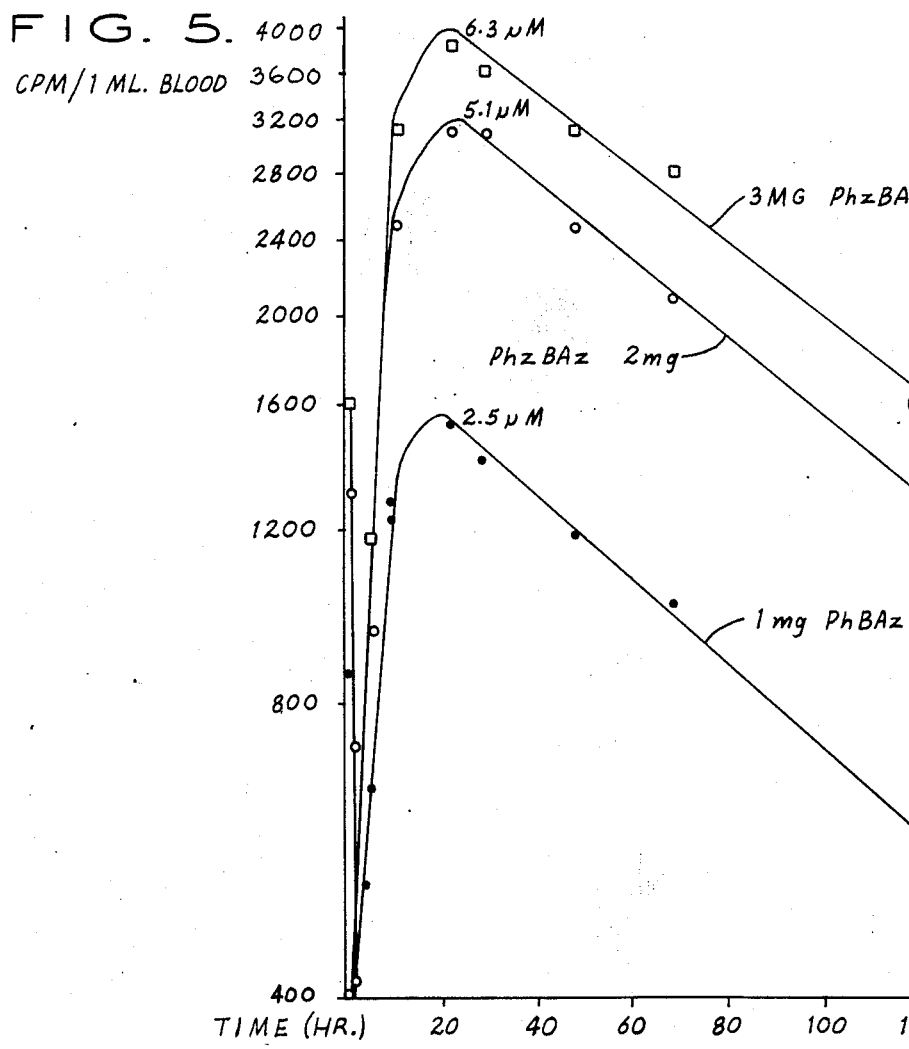

COMPOSITIONS AND METHOD OF TREATMENT FOR SICKLE CELL ANEMIA

TECHNICAL FIELD

This invention relates to the compound phlorizin benzylazide, pharmaceutical compositions thereof and their method of use for the treatment of sickle cell anemia.

BACKGROUND ART

Sickle cell anemia results from a defect in the genetic coding of the hemoglobin molecule. The abnormal hemoglobin S molecule in the red blood cells of sickle cell anemia patients is relatively insoluble and prone to deoxygenation-induced polymerization. When the sickle hemoglobin releases its oxygen at peripheral tissue sites, it undergoes aggregation which distorts the red cell's normal biconcave disc appearance and the characteristic spiculated, "holly leaf" or sickle shape is formed. This aberrant cell distortion accounts for the clinical problems in this disease, namely hemolytic anemia and vascular stasis, occlusion and thrombosis.

The viscosity of the red blood cell interior is largely a function of hemoglobin concentration. When cell water content falls, the deformability of the red blood cell decreases. This compromises the ability of the red blood cell to maneuver through the microvasculature of the body. This effect is magnified in the deoxygenated sickle red blood cell because the rate at which the hemoglobin S polymerizes is greatly accelerated by cellular dehydration, because aggregation is extremely dependent upon the deoxy-hemoglobin S concentration. There is also evidence that the sickle cell becomes dehydrated during deoxygenation and this initiates the cell sickling.

Additional research has indicated that a dysfunctional membrane of the sickle red blood cell plays a fundamental roll in disease pathophysiology. Studies indicate that the deformation or sickling process resulting from deoxygenation requires about 10–15 seconds to complete. Thus, it may be necessary for the blood in the microvasculature to slow abnormally before sickling of most cells occurs. This slowing could be induced because of abnormal interactions between the sickle cell and the micro-blood vessel wall due to an altered red blood cell membrane construction. There may also exist subpopulations of abnormally dense and inflexible red blood cells reflecting cellular dehydration and increased internal viscosity.

These features are presumed to be due to altered ion flux and homeostasis controlled by the cell membrane. Furthermore, when a cell sickles and unsickles repeatedly, the membrane is affected and the cell becomes irreversibly sickled, remaining deformed even when the hemoglobin S is reoxygenated in the lungs. These irreversibly sickled cells (hereinafter ISC) have a drastically reduced water content and, thus, high hemoglobin concentrations, as well as high calcium and low potassium content. They may also be ATP-depleted. ISC's have short intravascular life-spans and the severity of the hemolytic process is directly related to the number of these cells in a patient's circulation. Presumably, the permanently deformed cytoskeletons of the ISC's make them unable to negotiate through capillaries.

Based on the above evidence, researchers have sought a drug that would interact with the red blood cell membrane and increase sodium permeability and/or inhibit calcium uptake and potassium chloride plus water loss. Further, by preventing cellular dehydration, the drug would serve to preserve the deformability of the sickle red blood cell, prevent sickling, and be an extremely valuable therapeutic approach to the control of sickle cell anemia crisis.

As a result, a large variety of structurally and mechanistically dissimilar antisickling agents have been proposed for the treatment of sickle cell anemia. So far, however, none of these have been found to be clinically useful. Most inhibit red blood cell sickling either by chemically modifying the hemoglobin S molecule to prevent its aggregation or by increasing red blood cell affinity for oxygen. Approaches include the use of acetylators, such as aspirin; cross-linking agents, such as dimethyladipimidate; inhibitors of intra-molecular hydrophobic bonds, such as urea; and chemical group reactants, such as cyanate (as in U.S. Pat. No. 3,833,724 to Cerami et al).

Because of the critical role of hemoglobin S concentration in the sickling process, it has been proposed that even a modest reduction of mean cell hemoglobin concentration in the sickle cell will greatly decrease any propensity to sickle. Clinical trials in which sickle patients on a low sodium diet were given anti-diuretic hormone to reduce plasma $Na^+$-osmolality in hopes of producing a secondary reduction in cell hemoglobin S concentration had very limited success. Low plasma $Na^+$ levels simply could not be maintained. Further, this is an ineffective means of increasing red blood cell water content. Other investigators have used the antibiotic Monensin to induce a $Na^+$-selective leak in the red blood cell membrane. It was found that this $Na^+$-ionophore produced an influx of sodium salt and water into the sickle cell. This increased hydration produced some improvemement in the deformability of the red blood cell. Disadvantageously, however, Monensin is highly toxic in experimental animals at micromolar levels.

From the above, it is clear that a need exists for a safe, effective and clinically useful compound for the treatment of sickle cell anemia. During the course of experiments designed to photoaffinity label and identify the glucose transport carrier in normal human red blood cells, we found that phlorizin benzylazide caused hemolysis of the red blood cells under certain conditions. The phlorizin derivative has a high, but reversible, affinity for the sugar transporter in subdued light and is a potent inhibitor of the transfer mechanism. After allowing the compound to associate with its specific membrane receptor, activation with light was expected to result in relatively specific, covalent, irreversible labeling of the transporter. However, in our initial experiments, even before illumination, the red blood cells were found to swell and, in a time and drug dose-dependent manner, burst even in an isotonic buffer. These results suggested to us that this compound has potential usefulness as a membrane perturbant and antisickling agent. Further experiments were then conducted to demonstrate the safety and effectiveness of phlorizin benzylazide for use in a method of treating sickle cell anemia.

SUMMARY OF THE INVENTION

It is, accordingly, one object of the present invention to provide pharmaceutical compositions, including phlorizin benzylazide as an active ingredient, for the effective and safe treatment of sickle cell anemia.

A further object of the present invention is to provide a safe and effective method of use of phlorizin benzylazide containing compositions in treating sickle cell anemia.

Other objects and advantages of the present invention will become apparent as the description thereof proceeds.

In satisfaction of the foregoing objects and advantages, there is provided by this invention anti-sickling compositions comprising as the active ingredient an effective amount of the compound phlorizin benzylazide. Also provided are methods for administration of the anti-sickling compositions of this invention to patients suffering from sickle cell anemia and from the crisis episode of the disease. Preferably, the anti-sickling composition is administered in an intravenous load dosage of between 0.5-1.0 milligrams of the phlorizin benzylazide active ingredient per kilogram of the patient.

Since the active ingredient has an unusually long biological half-life of approximately 75 hours, maintenance dosages of from 0.05 to 0.2 milligrams of phlorizin benzylazide per kilogram of patient weight are then administered to the patient daily. This procedure advantageously serves to maintain an approximately 6–12.5 $\mu M$ concentration of phlorizin benzylazide (unbound) in the bloodstream of the patient. Phlorizin benzylazide at these concentration levels interacts with the red blood cell membrane, allowing salt and water to enter the cell under the osmotic drive of the impermeant hemoglobin. The additional salt and water swell the red blood cells to a spheroid shape and reduce the concentration of hemoglobin S below a critical concentration so that upon deoxygenation, sickling does not occur. Additionally, doses of phlorizin benzylazide effective to prevent sickling at this concentration cause few or no sickle cells to burst. Further, at potentially therapeutic doses, phlorizin benzylazide is not grossly toxic and, therefore, provides a relatively safe method for treating sickle cell anemia.

BRIEF DESCRIPTION OF THE DRAWINGS

FIG. 4 demonstrates how phlorizin benzylazide inhibits red blood cell sickling induced by deoxygenation.

FIG. 5 graphically depicts the absorption and elimination rate of phlorizin benzylazide in rats.

DETAILED DESCRIPTION OF THE INVENTION

Figure 1:
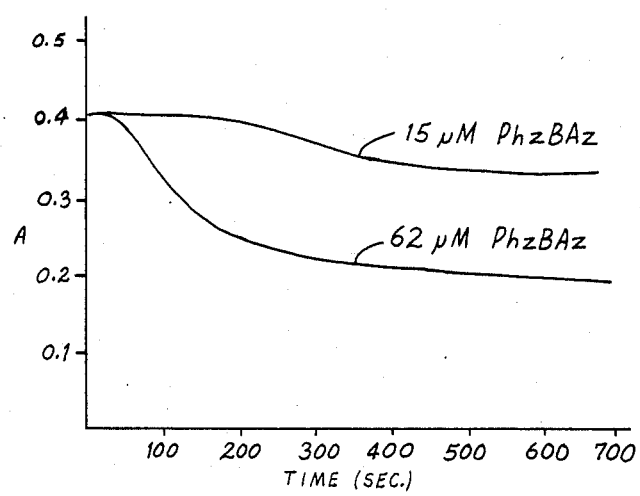
FIG. 1 graphically demonstrates the kinetics of phlorizin benzylazide-induced hemolysis.

As indicated above, the present invention is drawn to novel pharmaceutical compositions containing an effective amount of phlorizin benzylazide as the active ingredient. The compositions are useful in the method of the present invention for treating sickle cell anemia.

It is believed the structural features of phlorizin benzylazide allow it to interact with a component of the red blood cell membrane, possibly the glucose transporter. The phlorizin benzylazide distorts the glucose transporter or some other integral protein to form a micropore or seam between the membrane proteins and the lipid-bilayer of the membrane. Hemoglobin remains impermeant to this seam and, therefore, provides an osmotic force for water as well as salt to enter the red blood cell. This flux of water and salt serves to swell the red blood cell to a spheroid shape and reduce the concentration of hemoglobin S in the cell below a critical concentration, thereby preventing sickling or significantly delaying sickling until the hemoglobin S can again become oxygenated.

The pharmaceutical preparations or compositions of the present invention include an effective amount of the active ingredient phlorizin benzlyazide admixed with a pharmaceutical organic or inorganic excipient. Suitable excipients are substances that do not react with the novel inhibitory compounds. Specific examples of such excipients include water, peanut oil, olive oil or syrup. Of course, other known medicinal excipients may be used.

Preferably, the compositions are designed and adapted to be administered parenterally such as by subcutaneous depo injection or I.V. drip. Advantageously, this avoids the risks involved in oral administration wherein the phlorizin portion of the molecule could be hydrolyzed by the intestinal epithelia to phloretin. As is well known, phloretin readily enters the blood stream and causes at appropriate levels toxic effects at all sites in the body.

As more fully shown in the examples discussed below, an effective amount of the active ingredient is approximately a 6 to 12.5 $\mu M$ blood level concentration of phlorizin benzylazide. At this concentration level there is little or no cell lysis due to the incoming flux of water and salt across the cell membrane. It, however, should be recognized that higher concentration levels of phlorizin benzylazide could be used, for example, in an emergency to combat a sickle cell crisis. The higher concentrations are anticipated to be followed by a transfusion of whole blood to replace those red blood cells in the patient that burst under the influence of the phlorizin benzylazide and to bring the phlorizin benzylazide concentration level in the blood back down to a safer concentration range.

Thus, it should be appreciated that the method of treating sickle cell anemia includes the step of administering parenterally a load dosage of from 0.5–1.0 milligrams of phlorizin benzylazide per kilogram of patient weight. This, of course, may be done over a period of time intravenously or by one or more subcutaneous depo injections.

The higher end of the range is appropriate when seeking to combat the effects of sickle cell crisis with dosage levels above the range providing increased risk of side effects from red blood cell lysis. The lower end and middle portion of the load dosage range is appropriate when using phlorizin benzylazide as a prophylaxis with load dosages less than the range failing to provide satisfactory therapeutic or anti-sickling action. For example, a load dosage level of approximately 0.75 mg per kilogram of patient weight provides the patient with a blood concentration level of phlorizin benzylazide therapeutically effective in resisting hemolytic anemia and vascular stasis, occlusion and thrombosis associated with sickle cell anemia. Further, such load dosages bring the blood level concentration of phlorizin benzylazide in the patient to approximately the 6–12.5 $\mu M$ level, on the basis that the agent distributes solely in the extracellular fluid and is not sequestered in various body compartments. Advantageously, at this level, cell swelling and anti-sickling action are maximized with little or no red blood cell lysis occuring.

An additional advantage of the composition of the present invention is the unusually long biological half-life enjoyed by the phlorizin benzylazide. The half-life has been shown experimentally to be of approximately 75 hours. Thus, after the load dosage is administered, initial anti-sickling action is long lived and maintenance dosage to maintain the blood cell concentration level at approximately the 6–12.5 μM level is quite small. In particular, 0.05 to 0.2 milligrams of phlorizin benzylazide per kilogram of patient weight are required per day to continue to provide effective anti-sickling action to the patient. Again, it should be recognized that the higher end of the range is for combatting the effects of sickle cell crisis and the lower end and middle portion is for less severe periods of the affliction. For example, normally a maintenance dosage of approximately 0.125 mg of phlorizin benzylazide per kilogram of patient weight provides effective therapeutic action.

The following synthesis and examples are presented to further illustrate the invention, but it is not to be considered as limited thereto. In the examples, the formation of synthetic intermediates was monitored by thin layer chromatography performed on Silica Gel 60 F-254 plates using the solvent systems indicated. The structure of the isolated compounds was established spectrophotometrically. Proton-NMR spectra (100 MHz) were recorded on a Varian HA-100 Spectrometer using $(CH_3)_4Si$ (=0.00) as internal standard and acetone-$d_6$, acetic acid or trichlorosilene as solvents. Chemical shifts are given in ppm. Infra-red spectra were taken in KBr pellets on a Beckman IR-8 spectrometer and ultraviolet spectra on an Aminco DW-2a UV/VIS spectrophotometer.

Elemental and functional group analyses were performed by Galbraith Laboratories, Knoxville, TN and by the Laboratorium für Organische Chemie, Eidengenössische Technische Hochschule-Zentrum, Zürich, Switzerland.

Melting points were taken on a Thomas Hoover capillary melting point apparatus and are uncorrected.

Synthesis of Phlorizin Benzylazide

Phlorizin (7 mmol) and p-nitrobenzaldehyde (5 mmol) were dissolved in 84 ml methanol and cooled to 0° C. Under a nitrogen atmosphere, 14 meq of 1N KOH were added dropwise with magnetic stirring and the reaction was allowed to incubate for 2 hrs. at 0° C. and then 1.5 hrs. at 50° C. The reaction mixture was re-cooled to 0° C. and neutralized by the dropwise addition of 14 meq of 0.5N HCl. The solvent was removed in vacuo to yield a brown syrup containing primarily the presumed carbinol (carbinol was not sufficiently stable to be analyzed) and unreacted phlorizin. The mixture was dissolved in 10 ml $CHCl_3/CH_3OH$ (4:1) and subjected to flash chromatography on a column of Silica Gel 60 (4.5×26 cm) that had been pressure packed with chloroform. Elution was conducted with 0.75 L 15% methanol in chloroform, followed by 0.5 L 18% and then 0.5 L 22% of the same solvent mixture. Thin layer chromatography was used to monitor the fractionation: the eluate volume between 0.4–0.5 L contained essentially pure 2'-O-(β-D-gluco-pyranosyl)-5'-p-nitrobenzyl carbinol (hereinafter called GNC) (0.8 g, 20%) while the 0.5–1.4 L eluate contained 2.4 g of a mixture of GNC contaminated with approximately 20% phlorizin. $R_f$ value of the presumed compound GNC in 25% $MeOH/CHCl_3$ was 0.25.

Compound GNC (0.96 g in 100 ml methanol) was catalytically hydrogenated with 150 mg 10% Pd on charcoal for 1 hr at 22° C. at atmospheric pressure, and then 3 hr. at 55° C. at 30 cm $H_2O$ pressure. At lower temperatures reduction was incomplete and yielded an unstable orange product. The catalyst was removed and the methanol was evaporated in vacuo to yield crude phlorizin-5'-benzylamine (0.84 g, 92%). The product was dissolved in 8 ml methanol and mixed with 10 ml Sephadex G-10 slurry equilibrated in 50% methanol. Finally 8 ml $H_2O$ was added and the resulting slurry was added to the top of a Sephadex G-10 column (2.5× 27 cm) likewise equilibrated in 50% methanol. Elution was conducted with 0.8 L 50% methanol followed by 0.7 L 55% methanol and 1.0 L 60% methanol. The amine was eluted in the 1.1–2.0 L fraction. If the amine had been contaminated prior to this chromatography, phlorizin was readily separated at this step and could be recovered in the 0.36–0.66 L fraction. Phlorizin-5'-benzylamine was obtained by evaporating the solvent and crystallization from aqueous methanol as the monohydrate (0.55 g, 60%); after drying at 80° C. in vacuo its m.p. was 197°–200° C.

| Elemental Analysis: | | | |
|---|---|---|---|
| | C | H | N |
| Calculated for $C_{28}H_{31}O_{10}N.H_2O$: | 60.10 | 5.94 | 2.54 |
| Found for the reaction product: | 60.30 | 5.90 | 2.51 |

In order to verify that the reaction conditions were sufficient to reduce the secondary hydroxyl group of GNC, the phlorizin-5'-benzylamine reaction product was quantitatively acetylated with acetic anhydride in the presence of pyridine. Theoretical incorporation is 8 moles acetate/mole glycoside. Found for phlorizin-5'-benzylamine: 7.82 moles acetate/mole phlorizin-5'-benzylamine (97.8%).

An acetamide derivative of the reaction product prepared by coupling acetic acid and the amine in methanol with EDAC, was crystallized from 30% methanol as the monohydrate. After drying at 80° C. in vacuo its m.p. was: 215° C. after softening at 149° C.

| Elemental Analysis: | | | |
|---|---|---|---|
| | C | H | N |
| Calculated for $C_{30}H_{33}O_{11}N$: | 61.64 | 5.69 | 2.49 |
| Found for acetamide derivative of the reaction product: | 61.58 | 5.90 | 2.32 |

Further evidence confirming the compound to be phlorizin-5'-benzylamine was provided by comparing its proton NMR spectra with that of phlorizin. The $A_2B_2$ pattern at 2.88 and 3.50 ppm arising from the $-CH_2CH_2CO-$ moiety in phlorizin also appears at 2.87 and 3.49 ppm in the spectra of phlorizin-5'-benzylamine (in both compounds the triplet at 3.5 ppm is partially obscured by the signals arising from the protons in the glucose moiety). The B-ring AA'BB'-system at 6.72 and 7.10 ppm remained unchanged, but phlorizin's A-ring AB-system at 5.99 and 6.25 ppm was converted to a 1H singlet at 7.42 ppm in compound phlorizin-5'-benzylamine. The new C ring AA'BB' system in compound phlorizin-5-benzylamine gave signals at 6.54 and 6.98 ppm and the new —CH$_2$ group is seen as a 2H singlet at 3.72 ppm.

Since phlorizin benzylazide was expected to be photolabile, it was synthesized and isolated in subdued light. Cold 0.5N HCl (1.4 meq) was added slowly with magnetic stirring to 0.14 mmol of the phlorizin-5'-benzylamine in 8 ml acetone (−2° C.) followed by dropwise addition of 0.28 mmol NaNO$_2$ in 0.5 ml H$_2$O. The reaction mixture was stirred for 5 min and then 1.4 mmol NaN$_3$ (in 1 ml H$_2$O) was added. After 10 minutes excess urea was added with stirring. Acetone was then removed in vacuo and the product azide was precipitated from the reaction mixture by slow addition of ice cold H$_2$O. The isolated material was recrystallized from 15 ml 30% aqueous methanol to yield small white crystals as the monhydrate (0.053 g, 60%) with the following m.p.: softens at 115° C., discolors 205° C., decomposes >250° C. $R_f$=0.44 in chloroform/methanol, 7:3.

The infra-red spectra possessed the sharp 2120 cm$^{-1}$ and 1280 cm$^{-1}$ absorption peaks characteristic of an azide group. It has two major UV absorption maxima in ethanol or water; one at 255 nm attributable to the azide group, and the second at 280 nm which shifts to 334 nm in 0.05M sodium borate, pH 9.3 (334=2.95×10$^4$ cm$^{-1}$ M$^{-1}$, 255=2.35×10$^4$ cm$^{-1}$ M$^{-1}$.

EXAMPLE 1

Human red blood cells were obtained by venepuncture into Na citrate or EDTA vacutainers. They were used directly or stored in serum at 4° C. for various times. Serum and leucocytes were removed by siphoning and the settled red blood cells were washed once and finally made to a 0.15% suspension with isotonic NaCl containing 5 mM KH$_2$PO$_4$ (pH 6.2). These cells were kept at 2° C. for selected periods of time during a first incubation. From this point on, all experiments were performed in subdued light to protect the light-sensitive phlorizin benzylazide. The phlorizin benzylazide obtained from the synthesis described above was added at the desired concentrations, and during this variable temperature second incubation (2°–4° C. in presence of phlorizin benzylazide), the turbidity of the cell suspension was monitored at 610 nm with a continuously recording spectrophotometer to measure hemolysis. A relatively constant level of absorbance of light indicates decreased hemolysis occurring at the lower dosage and this was verified by concomitant counting of cells with a hemacytometer. Some typical data are shown in FIG. 1 showing the change in absorbance of light (note axis A) when the drug was added (at zero time). The higher level of Phlorizin Benzylazide caused not only a greater percentage of cell lysis (an absorbance of 0.087 represents 100% lysis) but the rate at which the cells burst was much faster.

Figure 2:
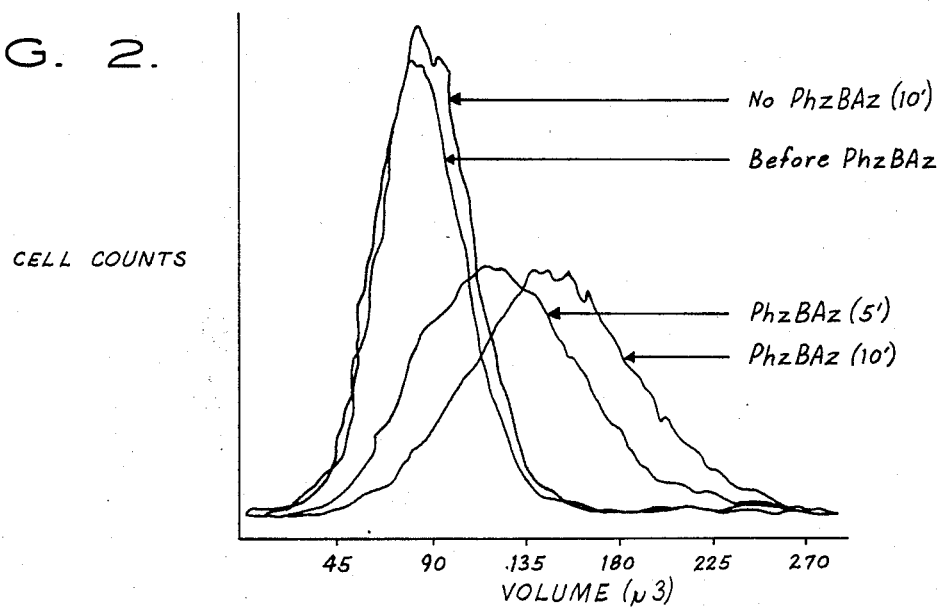
FIG. 2 graphically shows that phlorizin benzylazide causes an increase in intracellular volume of red blood cells.

Evidence that lysis is preceded by a progressive swelling of the red cell is shown in FIG. 2. In these experiments (n=2) red cells had been stored in serum for 30 hours, and experienced a first incubation for 60 min at 4° C. and a second incubation with 12.5 μM phlorizin benzylazide at 4° C. for 5 and 10 min. The integrated curves show that untreated red cells, with or without a 10 min incubation #2, have a mean volume of about 80 μ$^3$. When the compound is added, a time dependent increase in mean cell volume occurs with essentially no lysis within this time span (area under the curve remained unchanged). The Coulter Counter, an automated instrument which determines the number and volume of cells passing through an analysis chamber, was used to make these measurements.

Figure 3:
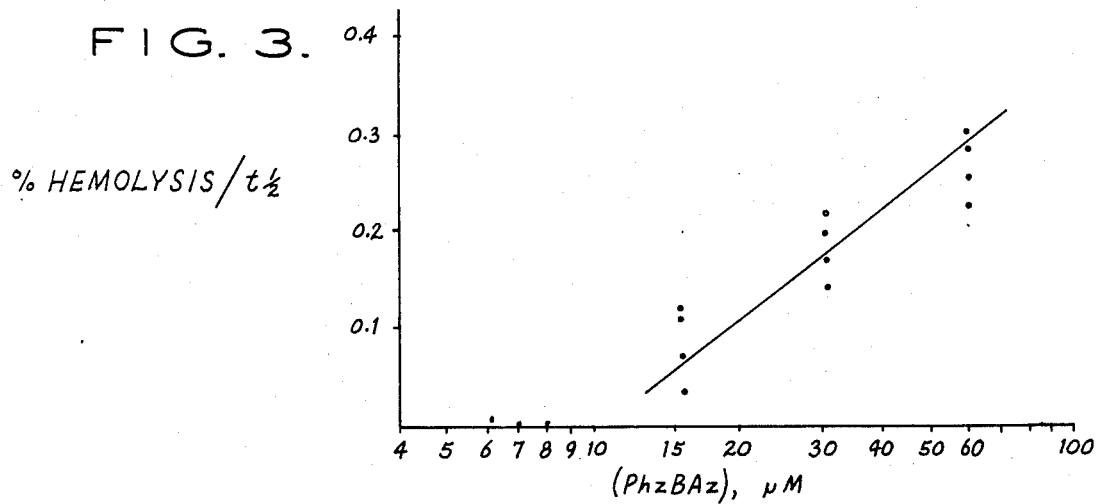
FIG. 3 shows that red blood cell swelling and lysis are dependent upon the concentration of phlorizin benzylazide present.

The dose-response curve of phlorizin benzylazide acting as a hemolytic agent of normal cells is shown in FIG. 3 and the following table:

| Phlorizin Benzylazide, κ M | % Hemolysis | t$_{\frac{1}{2}}$ |
| --- | --- | --- |
| 62 | 66 ± 8 | 233 |
| 31 | 41 ± 9.6 | 260 |
| 16 | 31 ± 8.6 | 450 |
| 8 | 0 | — |
| 4 | 0 | — |

In FIG. 3, potency is expressed as the ratio, % hemolysis/t$_{\frac{1}{2}}$, where t$_{\frac{1}{2}}$ represents the time (seconds) required to achieve 50% of the total hemolysis produced by the particular concentration of the compound within the time of our measurements (700 sec). The cells used for these experiments were 2 hours old, and subjected to an incubation for 30 minutes before the addition of phlorizin benzylazide and continuing thereafter at approximately 4° C. (n=4). Advantageously, cell swelling occurred at low phlorizin benzylazide levels and no cell lysis was observed at concentrations below 10 μM. Thus, this blood level concentration provides anti-sickling action by reducing the concentration of hemoglobin S with an influx of water and/or salt into the cells. Further, this is accomplished with little or no red blood cell lysis and, therefore, minimum adverse side effects.

EXAMPLE 2

This example demonstrates that phlorizin benzylazide inhibits sickling induced by deoxygenation in vitro. Whole blood was obtained from several volunteer sickle cell disease patients and was stored for several days at 4° C. However, for these experiments, the cells did not experience a cold incubation. Instead, whole blood was diluted into pre-warmed (37° C.) isotonic phosphate-buffered saline (± phlorizin benzylazide, 12.5 μM) which was then deoxygenated by continuous passage of an 100% Argon stream (1 liter/min) over a rotating thin film of the suspended cells. Aliquots were periodically taken, without O$_2$ exposure, and fixed in 1% glutaraldehyde. These samples were then examined under phase microscopy for the degree of sickling by counting fields of at least 100 cells using a single blind, experimental protocol.

The data shown in FIG. 4 illustrate that without phlorizin benzylazide present, about 35–40% of the cells from these patients assumed the typical sickle shape (only cells having a 3:1, length:width ratio were considered to be sickled); whereas, with the phlorizin benzylazide, the deoxygenation caused a maximum increase of 5% more than the 10% of cells already sickled at zero time. Actually, the effect of phlorizin benzylazide is even more dramatic. In the absence of phlorizin benzylazide, bizarre shape changes occurred in almost 100% of the cells when O$_2$ tension was lowered; whereas, with the phlorizin benzylazide, a uniform spherocytosis was induced in most cells. The 10–15% sickled cells present at zero time are probably the so-called irreversibly sickled cells (ISC). It should be emphasized that no significant hemolysis occurred in Example 2.

EXAMPLE 3

An animal study was then conducted to determine the absorption and elimination and characteristics of the phlorizin benzylazide and the resulting level of safety. Three adult rats of approximately 450 grams each were injected intraperitoneally at zero time in 1, 2 and 3 mg doses of tritiated phlorizin benzylazide (875,000 cpm/mg). Thereafter, serial tail blood samples were taken at varying times and analyzed for tritium. Maximal absorption of the compound from the peritoneal compartment was slow (note FIG. 5) and maximum blood level concentrations were obtained only after about 20 hours. The initial very rapid entry and elimination of a small fraction of the radioactivity was probably tritiated $H_2O$ and other radioactive impurities. Peak concentrations of the agent in the blood were reached at identical times in the three animals and were 2.5, 5.1 and 6.3 $\mu M$, roughly proportional to the dose administered. The absorption rate constant was estimated to be 0.07 $hr^{-1}$. Elimination of the drug was a first order process and the mean half life was an unusually long 75 hours as described above. This feature could, of course, offer advantages for therapy in a sickle cell crisis wherein long term effectiveness is desired. The animal receiving the lowest dosage was sacrificed after 5 days while the other two were observed for a period of 7 weeks. None of the animals exhibited any unusual behavioral abnormalities. Gross examination of all tissues were unremarkable and histological examination of the liver and kidney from the two older animals showed no pathology.

In summary, numerous benefits have been described which result from employing the concepts of the present invention. A novel pharmaceutical composition including an effective amount of the active ingredient phlorizin benzylazide is disclosed. The compositions are useful in a method for treating sickle cell anemia. Advantageously, the compositions serve to lower the hemoglobin S concentrations in the red blood cells of sickle cell anemia victims and, thereby, prevent sickling. As a further advantage, the biological half-life of the phlorizin benzylazide is approximately 75 hours. Therefore, the compositions provide a patient, particularly when undergoing sickle cell anemia crisis, with safe and effective long term anti-sickling action. Further, only minor maintenance dosages of the phlorizin benzylazide are required to maintain the anti-sickling action over a still longer period.

The invention has been described herein with reference to a certain preferred pharmaceutical composition embodiment. However, as obvious variations thereon will become apparent to those skilled in the art, the invention is not to be considered as limited thereto.

We claim:

1. A pharmaceutical composition for use in the treatment of sickle cell anemia patients comprising as an active ingredient an effective amount of phlorizin benzylazide.

2. The composition set forth in claim 1, including a pharmaceutical excipient so as to be adapted for administration parenterally.

3. The composition set forth in claim 1, in load dosage form including from 0.5-1.0 mg of active ingredient per kilogram of the patient.

4. The composition set forth in claim 3, wherein said load dosage is approximately 0.75 mg of active ingredient per kilogram of the patient.

5. The composition set forth in claim 1, in maintenance dosage form including from 0.05 to 0.2 mg of active ingredient per kilogram of the patient per day.

6. The composition set forth in claim 5, wherein said maintenance dosage is approximately 0.125 mg of active ingredient per kilogram of the patient per day.

7. The composition set forth in claim 1, wherein said effective amount of said active ingredient is approximately a 6-12.5 $\mu M$ concentration of phlorizin benzylazide in the blood of the patient.

8. A method for the treatment of sickle cell anemia in a patient comprising administering to the patient an effective dosage amount of phlorizin benzylazide.

9. The method of claim 8 wherein said effective dosage amount of phlorizin benzylazide is administered parenterally in a pharmaceutical excipient as a composition.

10. The method of claim 8, including the step of administering a load dosage to the patient of from 0.5-1.0 mg of phlorizin benzylazide per kilogram of the patient.

11. The method of claim 10, wherein said load dosage is approximately 0.75 mg of phlorizin benzylazide per kilogram of the patient.

12. The method of claim 8, including the step of administering a maintenance dosage to the patient of from 0.05 to 0.2 mg of phlorizin benzylazide per kilogram of the patient per day.

13. The method of claim 12, wherein said maintenance dosage is approximately 0.125 mg of phlorizin benzylazide per kilogram of the patient per day.

14. The method of claim 8, including the step of maintaining a phlorizin benzylazide concentration of approximately 6-12.5 $\mu M$ in the blood of the patient to inhibit cell sickling.

* * * * *